United States Patent
Tucciarone et al.

(10) Patent No.: US 7,713,293 B2
(45) Date of Patent: May 11, 2010

(54) TRANSVERSE SUSPENSION DEVICE

(75) Inventors: Agostino Tucciarone, Rome (IT); Simon David Mifsud, West Midlands (GB)

(73) Assignee: ArthroCare Corporation, Austin, TX (US)

(*) Notice: Subject to any disclaimer, the term of this patent is extended or adjusted under 35 U.S.C. 154(b) by 19 days.

(21) Appl. No.: 10/822,101

(22) Filed: Apr. 8, 2004

(65) Prior Publication Data

US 2004/0193167 A1 Sep. 30, 2004

(30) Foreign Application Priority Data

Apr. 15, 2003 (WO) .................... PCT/GB03/01606

(51) Int. Cl.
*A61B 17/86* (2006.01)
*A61F 2/08* (2006.01)
(52) U.S. Cl. ............... 606/321; 623/13.14; 606/304
(58) Field of Classification Search ... 623/13.11–13.14; 606/72
See application file for complete search history.

(56) References Cited

U.S. PATENT DOCUMENTS

| | | | |
|---|---|---|---|
| 1,727,590 A | 9/1929 | Thomas | 411/430 |
| 2,778,357 A | 1/1957 | Leibinger et al. | 128/2 |
| 3,896,500 A | 7/1975 | Rambert et al. | 623/13.14 |
| 3,905,356 A | 9/1975 | Fletcher et al. | 600/587 |
| 3,973,277 A | 8/1976 | Semple et al. | 623/13.14 |
| 3,974,621 A | 8/1976 | Stang | 411/75 |
| 4,126,165 A | 11/1978 | Guignard et al. | 142/56 |
| 4,149,277 A | 4/1979 | Bokros | 623/13.2 |
| 4,187,558 A | 2/1980 | Dahlen et al. | 623/13.14 |
| 4,204,544 A | 5/1980 | Feldstein et al. | 600/375 |
| 4,275,717 A | 6/1981 | Bolesky | 606/63 |
| 4,309,778 A | 1/1982 | Buechel et al. | 623/20.29 |
| 4,335,715 A | 6/1982 | Kirkley | 606/87 |
| 4,347,024 A | 8/1982 | Coldren | 411/11 |
| 4,406,281 A | 9/1983 | Hubbard et al. | 128/846 |
| 4,530,357 A | 7/1985 | Pawloski et al. | 606/180 |
| 4,573,448 A | 3/1986 | Kambin | 606/170 |

(Continued)

FOREIGN PATENT DOCUMENTS

DE    9002844    1/1991

(Continued)

OTHER PUBLICATIONS

PCT Notification of the International Search Report and Written Opninon for PCT/US06/19100, 7 pgs, Mailed Sep. 27, 2007.

(Continued)

*Primary Examiner*—Eduardo C Robert
*Assistant Examiner*—Mary Hoffman
(74) *Attorney, Agent, or Firm*—Matthew Scheele; Brian E. Szymczak

(57) ABSTRACT

A transverse suspension device for ACL graft fixation in a femoral tunnel includes a body section and a smooth head section forming the leading end of the device. The body and smooth head sections each may be cannulated along their entire lengths. The head section may further include a recess-engaging section extending proximally from the distal end and is operable to engage with a recess formed in the bone tunnel. The device may further include a graft loop support section between the recess-engaging section and the body section adapted to stably support the graft loop.

15 Claims, 9 Drawing Sheets

U.S. PATENT DOCUMENTS

| | | | | |
|---|---|---|---|---|
| 4,583,554 A | 4/1986 | Mittelman et al. | ........... | 600/587 |
| 4,600,005 A | 7/1986 | Hendel | ........ | 128/304 |
| 4,600,007 A | 7/1986 | Lahodny et al. | ............. | 606/174 |
| 4,708,132 A | 11/1987 | Silvestrini | .................... | 606/66 |
| 4,712,542 A | 12/1987 | Daniel et al. | ................... | 606/96 |
| 4,776,851 A | 10/1988 | Bruchman et al. | ........ | 623/13.11 |
| 4,820,279 A | 4/1989 | Dedo | ........................ | 604/290 |
| 4,910,901 A | 3/1990 | Boyar | .......................... | 40/607 |
| 4,950,270 A | 8/1990 | Bowman et al. | ............... | 606/72 |
| 4,969,471 A | 11/1990 | Daniel et al. | ................. | 600/587 |
| 4,997,433 A | 3/1991 | Goble et al. | ................... | 606/64 |
| 5,037,422 A | 8/1991 | Hayhurst et al. | ............... | 606/72 |
| 5,037,426 A | 8/1991 | Goble et al. | ................... | 606/96 |
| 5,046,513 A | 9/1991 | Gatturna et al. | ................ | 128/898 |
| 5,112,338 A | 5/1992 | Anspach, III | ................ | 606/99 |
| 5,139,520 A | 8/1992 | Rosenberg | ................... | 606/87 |
| 5,147,361 A | 9/1992 | Ojima et al. | ................... | 606/61 |
| D330,591 S | 10/1992 | Rosenberg et al. | ......... | D24/147 |
| 5,152,790 A | 10/1992 | Rosenberg et al. | ....... | 623/13.14 |
| 5,170,800 A | 12/1992 | Smith et al. | ................. | 600/564 |
| 5,176,682 A | 1/1993 | Chow | ........................... | 606/72 |
| 5,176,699 A | 1/1993 | Markham | .................... | 606/206 |
| 5,228,448 A | 7/1993 | Byrd | ........................... | 600/490 |
| 5,251,646 A | 10/1993 | Bowen | ........................ | 128/878 |
| 5,254,129 A | 10/1993 | Alexander | .................... | 606/170 |
| 5,258,003 A | 11/1993 | Ciaglia et al. | ................. | 606/185 |
| 5,258,016 A | 11/1993 | DiPoto et al. | ................. | 606/232 |
| 5,266,075 A | 11/1993 | Clark et al. | .................... | 606/138 |
| 5,303,472 A | 4/1994 | Mbanugo | ..................... | 30/124 |
| 5,306,301 A | 4/1994 | Graf et al. | .................... | 623/13 |
| 5,314,429 A | 5/1994 | Goble | .......................... | 606/96 |
| 5,324,308 A | 6/1994 | Pierce | ........................ | 606/232 |
| 5,330,468 A | 7/1994 | Burkhart | ..................... | 606/96 |
| 5,350,380 A | 9/1994 | Goble et al. | ................... | 606/80 |
| 5,350,383 A | 9/1994 | Schmieding et al. | .......... | 606/96 |
| 5,364,400 A | 11/1994 | Rego, Jr. et al. | | |
| 5,383,471 A | 1/1995 | Funnell | ....................... | 600/564 |
| 5,391,169 A | 2/1995 | McGuire | ..................... | 606/79 |
| 5,393,302 A | 2/1995 | Clark et al. | .................... | 606/72 |
| RE34,871 E | 3/1995 | McGuire et al. | .............. | 606/73 |
| 5,395,375 A | 3/1995 | Turkel et al. | .................. | 606/83 |
| 5,405,359 A | 4/1995 | Pierce | ........................ | 606/232 |
| 5,408,359 A | 4/1995 | Ferrett et al. | ................. | 359/601 |
| 5,423,860 A | 6/1995 | Lizardi et al. | ................. | 606/232 |
| 5,472,452 A | 12/1995 | Trott | ........................ | 606/232 |
| 5,475,553 A | 12/1995 | Saliba | ........................ | 360/122 |
| 5,489,292 A | 2/1996 | Tovey et al. | .................. | 606/207 |
| 5,529,424 A | 6/1996 | Neubert et al. | .............. | 403/298 |
| 5,556,411 A | 9/1996 | Taoda et al. | .................. | 606/185 |
| 5,562,664 A | 10/1996 | Durlacher et al. | ............. | 606/96 |
| 5,591,190 A | 1/1997 | Yoon | .......................... | 606/185 |
| 5,591,232 A | 1/1997 | Rahimi et al. | ................. | 128/898 |
| 5,601,562 A * | 2/1997 | Wolf et al. | .................... | 606/86 |
| 5,609,634 A | 3/1997 | Voydeville | ............... | 623/13.11 |
| 5,618,314 A | 4/1997 | Harwin et al. | ............... | 606/232 |
| 5,620,001 A | 4/1997 | Byrd et al. | .................... | 606/202 |
| 5,626,609 A | 5/1997 | Zvenyatsky et al. | ......... | 606/208 |
| 5,632,748 A | 5/1997 | Beck et al. | .................... | 606/89 |
| 5,643,266 A | 7/1997 | Li | ................................ | 606/72 |
| 5,643,273 A | 7/1997 | Clark | .......................... | 606/96 |
| 5,645,588 A | 7/1997 | Graf et al. | .................... | 606/151 |
| 5,647,874 A | 7/1997 | Hayhurst | ..................... | 606/72 |
| 5,651,368 A | 7/1997 | Napolitano et al. | ......... | 600/490 |
| 5,674,224 A * | 10/1997 | Howell et al. | ................. | 606/88 |
| 5,683,359 A | 11/1997 | Farkas et al. | ................. | 604/22 |
| 5,683,471 A | 11/1997 | Incavo et al. | ................ | 128/898 |
| 5,707,395 A | 1/1998 | Li | .............................. | 606/232 |
| 5,713,897 A | 2/1998 | Goble et al. | ................... | 606/53 |
| 5,725,541 A | 3/1998 | Anspach et al. | .............. | 606/151 |
| 5,733,307 A | 3/1998 | Dinsdale | ..................... | 606/232 |
| 5,735,867 A | 4/1998 | Golser et al. | ................. | 606/185 |
| 5,769,894 A | 6/1998 | Ferragamo | ................... | 606/148 |
| 5,782,749 A | 7/1998 | Riza | ........................... | 600/117 |
| 5,788,701 A | 8/1998 | McCue | ......................... | 606/88 |
| 5,791,350 A | 8/1998 | Morton | ....................... | 600/590 |
| 5,797,963 A | 8/1998 | McDevitt | .................... | 606/232 |
| 5,813,808 A | 9/1998 | Wu | ............................. | 411/32 |
| 5,814,070 A | 9/1998 | Borzone et al. | ............. | 606/232 |
| 5,840,078 A | 11/1998 | Yerys | ......................... | 606/151 |
| 5,871,504 A | 2/1999 | Eaton et al. | .................. | 606/232 |
| 5,891,150 A | 4/1999 | Chan | .......................... | 606/96 |
| 5,891,168 A | 4/1999 | Thai | ........................... | 606/232 |
| 5,895,425 A * | 4/1999 | Grafton et al. | ................ | 606/73 |
| 5,911,695 A | 6/1999 | Watkins et al. | .............. | 600/553 |
| 5,913,860 A | 6/1999 | Scholl | ........................ | 606/100 |
| 5,918,604 A | 7/1999 | Whelan | ....................... | 128/898 |
| 5,935,129 A | 8/1999 | McDevitt et al. | ............. | 606/72 |
| 5,984,966 A | 11/1999 | Kiema et al. | ............. | 623/13.14 |
| 5,989,253 A | 11/1999 | Bigliardi | ...................... | 606/72 |
| 6,015,412 A | 1/2000 | Mifsud | ........................ | 606/83 |
| 6,056,752 A | 5/2000 | Roger | ...................... | 623/13.12 |
| 6,068,648 A | 5/2000 | Cole et al. | ................... | 606/232 |
| D426,305 S | 6/2000 | Hein | .......................... | D24/147 |
| 6,080,154 A | 6/2000 | Reay-Young et al. | ......... | 606/60 |
| 6,086,591 A | 7/2000 | Bojarski | ...................... | 606/64 |
| 6,099,568 A | 8/2000 | Simonian et al. | ......... | 623/13.11 |
| 6,110,207 A | 8/2000 | Eichhorn et al. | ......... | 623/13.14 |
| 6,117,161 A | 9/2000 | Li et al. | ...................... | 606/232 |
| 6,132,433 A | 10/2000 | Whelan | ........................ | 606/72 |
| 6,146,406 A | 11/2000 | Shluzas et al. | .............. | 606/232 |
| 6,146,407 A | 11/2000 | Krebs | ......................... | 606/232 |
| 6,152,928 A | 11/2000 | Wenstrom | .................... | 606/72 |
| 6,156,039 A | 12/2000 | Thal | ........................... | 606/72 |
| 6,187,011 B1 | 2/2001 | Torrie | ......................... | 606/96 |
| 6,214,007 B1 | 4/2001 | Anderson | ..................... | 606/73 |
| 6,221,107 B1 | 4/2001 | Steiner et al. | ............. | 623/13.14 |
| 6,224,603 B1 | 5/2001 | Marino | ........................ | 606/79 |
| 6,254,606 B1 | 7/2001 | Carney et al. | ............... | 606/102 |
| 6,306,138 B1 * | 10/2001 | Clark et al. | .................... | 606/65 |
| 6,319,270 B1 | 11/2001 | Grafton et al. | .............. | 606/232 |
| 6,328,758 B1 | 12/2001 | Tornier et al. | ............... | 606/232 |
| 6,355,053 B1 | 3/2002 | Li | .............................. | 606/232 |
| 6,355,066 B1 | 3/2002 | Kim | ......................... | 623/13.14 |
| 6,371,124 B1 * | 4/2002 | Whelan | ....................... | 128/898 |
| 6,379,361 B1 | 4/2002 | Beck, Jr. et al. | ............... | 606/72 |
| 6,402,757 B1 | 6/2002 | Moore, III et al. | ............ | 606/80 |
| 6,440,134 B1 | 8/2002 | Zaccherotti et al. | ........... | 606/62 |
| 6,478,753 B2 | 11/2002 | Reay-Young | ............... | 600/595 |
| 6,491,714 B1 | 12/2002 | Bennett | ...................... | 606/232 |
| 6,499,486 B1 * | 12/2002 | Chervitz et al. | ............. | 128/898 |
| 6,517,542 B1 | 2/2003 | Papay et al. | .................. | 606/232 |
| 6,517,578 B2 | 2/2003 | Hein | ......................... | 623/13.13 |
| 6,527,795 B1 | 3/2003 | Lizardi | ........................ | 606/232 |
| 6,533,802 B2 | 3/2003 | Bojarski et al. | .............. | 606/232 |
| 6,533,816 B2 | 3/2003 | Sklar | ........................ | 623/13.14 |
| 6,544,273 B1 | 4/2003 | Harari et al. | ................. | 606/151 |
| 6,547,800 B2 | 4/2003 | Foerster et al. | .............. | 606/151 |
| 6,551,343 B1 | 4/2003 | Tormala et al. | .............. | 606/213 |
| 6,554,553 B2 | 4/2003 | Freedland | .................... | 411/392 |
| 6,562,071 B2 | 5/2003 | Jarvinen | ................... | 623/13.14 |
| 6,599,289 B1 | 7/2003 | Bojarski et al. | ............... | 606/60 |
| 6,610,064 B1 * | 8/2003 | Goble et al. | ................... | 606/72 |
| 6,610,080 B2 | 8/2003 | Morgan | ....................... | 606/232 |
| 6,623,524 B2 * | 9/2003 | Schmieding | ............. | 623/13.14 |
| 6,635,074 B2 | 10/2003 | Bartlett | ....................... | 606/232 |
| 6,652,533 B2 | 11/2003 | O'Neil | ........................ | 606/100 |
| 6,652,560 B1 | 11/2003 | Gerke et al. | .................. | 606/232 |
| 6,685,728 B2 | 2/2004 | Sinnott et al. | ............... | 606/232 |
| 6,736,847 B2 | 5/2004 | Seyr et al. | ................. | 623/13.14 |
| 6,780,188 B2 * | 8/2004 | Clark et al. | .................... | 606/73 |
| 6,802,862 B1 | 10/2004 | Roger et al. | ............... | 623/13.14 |
| 6,808,528 B2 | 10/2004 | Justin | ......................... | 606/72 |
| 6,878,166 B2 * | 4/2005 | Clark et al. | ................. | 623/13.12 |
| 6,905,513 B1 * | 6/2005 | Metzger | ..................... | 623/20.17 |

| | | | |
|---|---|---|---|
| 6,991,631 | B2 | 1/2006 | Woloszko et al. ............ 606/41 |
| 6,994,725 | B1* | 2/2006 | Goble .................... 623/13.14 |
| 7,001,429 | B2 | 2/2006 | Ferguson ................ 623/13.14 |
| 7,063,717 | B2 | 6/2006 | St. Pierre et al. ............ 606/232 |
| 7,083,647 | B1 | 8/2006 | Sklar et al. ............... 623/13.14 |
| 7,226,469 | B2 | 6/2007 | Benavitz et al. ............ 606/232 |
| D547,451 | S | 7/2007 | Asfora ..................... D24/146 |
| 7,285,121 | B2 | 10/2007 | Braun et al. ............... 606/279 |
| 7,338,492 | B2 | 3/2008 | Singhatat et al. ........... 606/232 |
| 2001/0044627 | A1* | 11/2001 | Justin ......................... 606/72 |
| 2002/0038123 | A1 | 3/2002 | Visotsky et al. ............. 606/73 |
| 2004/0049195 | A1* | 3/2004 | Singhatat et al. ............ 606/72 |
| 2005/0075636 | A1 | 4/2005 | Gotzen ....................... 606/72 |
| 2005/0192582 | A1 | 9/2005 | Reay-Young ............... 606/79 |
| 2005/0222619 | A1 | 10/2005 | Dreyfuss et al. ............. 606/72 |
| 2006/0178673 | A1 | 8/2006 | Curran ..................... 606/100 |
| 2006/0235516 | A1 | 10/2006 | Cavazzoni | |
| 2006/0253119 | A1 | 11/2006 | Berberich et al. ............ 606/72 |
| 2006/0271059 | A1 | 11/2006 | Reay-Young et al. ......... 606/96 |
| 2006/0276841 | A1 | 12/2006 | Barbieri et al. ............. 606/232 |
| 2007/0021751 | A1 | 1/2007 | Reay-Young et al. ......... 606/72 |
| 2007/0213730 | A1 | 9/2007 | Martinek et al. ............. 606/72 |
| 2007/0260249 | A1 | 11/2007 | Boyajian et al. ............. 606/72 |
| 2008/0275553 | A1 | 11/2008 | Wolf et al. ............... 623/13.14 |
| 2008/0288069 | A1 | 11/2008 | Wolf et al. ................. 606/301 |

FOREIGN PATENT DOCUMENTS

| | | |
|---|---|---|
| DE | 29607352 | 9/1996 |
| EP | 238223 | 9/1987 |
| EP | 279129 | 8/1988 |
| EP | 317406 | 5/1989 |
| EP | 379789 | 11/1989 |
| EP | 346469 | 12/1989 |
| EP | 574707 | 12/1993 |
| EP | 619982 | 3/1994 |
| EP | 0 674 880 | 3/1995 |
| EP | 0674880 | 3/1995 |
| EP | 706780 | 4/1996 |
| EP | 0865774 | 9/1998 |
| EP | 1066805 | 6/2000 |
| EP | 1180351 | 2/2002 |
| FR | 2395012 | 1/1979 |
| FR | 2590792 | 6/1987 |
| FR | 2683715 | 5/1993 |
| FR | 2725615 | 4/1996 |
| FR | 2732211 | 4/1996 |
| GB | 2288739 | 11/1995 |
| GB | 2337463 | 11/1999 |
| SU | 1521465 | 11/1989 |
| WO | 93/25148 | 12/1993 |
| WO | 95/11631 | 5/1995 |
| WO | 96/03926 | 2/1996 |
| WO | 96/29029 | 9/1996 |
| WO | 96/39934 | 12/1996 |
| WO | 97/19634 | 6/1997 |
| WO | 97/20522 | 6/1997 |
| WO | 98/12991 | 4/1998 |
| WO | 98/12992 | 4/1998 |
| WO | 98/22048 | 5/1998 |
| WO | 98/38937 | 9/1998 |
| WO | 99/52472 | 10/1999 |
| WO | 99/59488 | 11/1999 |
| WO | 03/088874 | 10/2003 |
| WO | WO03-088874 | 10/2003 |

OTHER PUBLICATIONS

PCT Notification of the International Search Report and Written Opninon for PCT/US05/17382, 11 pgs, Mailed Oct. 23, 2007.
PCT Notification of the International Search Report and Written Opninon for PCT/US05/01629, 6 pgs, Mailed Apr. 22, 2008.
Smith & Nephew, "Arthroscopic Repair of a Bankart Lesion Using TAG Suture Anchors," 12 pgs, May 1996.
F.H. Fuh, et al., Anatomic ACL Double-Bundle Reconstruction, Orthopedic Technology Review vol. 7 No. 4, 6 pgs, 2005.
ArthroCare SportsMedicine Product Catalogue, 3.1 Knee (p. 44 p. 52), 4 pgs, Jul. 2005.
UK Search Report for GB 9915550 1 pg, Jun. 13, 2000.
UK Search Report for GB 9929599 1 pg, Oct. 12, 2000.
UK Search Report for GB 0116605 1 pg, Mar. 27, 2002.
UK Search Report for GB 0013037 1 pg, Mar. 20, 2001.
UK Search Report for GB 0208667 1 pg, Feb. 24, 2003.
European Search Report for EP 00113471 2 pgs, Jan. 26, 2001.
European Search Report for EP 00311077 2 pgs, Mar. 6, 2001.
European Search Report for EP 00830524 2 pgs, Aug. 8, 2001.
European Search Report for EP 01112516 2 pgs, Aug. 7, 2003.
European Search Report for EP 02013879 4 pgs, May 25, 2004.
European Search Report for EP 02014485 2 pgs, Nov. 4, 2003.
European Search Report for EP 97122626 2 pgs, Apr. 21, 1998.
European Search Report for EP 98301702 2 pgs, Jun. 23, 1998.
European Search Report for EP 99302529 2 pgs, Jul. 8, 1999.
PCT International Search Report for PCT/GB03/01606 3 pgs, Mailed Sep. 4, 2003.
PCT International Search Report for PCT/US06/04674 1 pg, Mailed Jul. 25, 2007.
PCT Written Opinion for PCT/US06/04674 4 pgs, Mailed Jul. 25, 2007.
"Graft Choices in ACL Reconstruction", Carleton Sports Medicine, <www.carletonsportsmed.com/graftacl.htm>, Printed Aug. 21, 2006.
"Distal Tendon Repair with the Lubbers Technique", Ortheon Medical, <www.ortheon.com/distal.htm>, Printed Aug. 21, 2006.
Daily Updates, "ACL Reconstruction Using a Double-Looped Semitendinous and Gracilis (DLSTG) Hamstring Graft with the Bone Much Screw and Sasherloc Device from Arthrotec", <www.ptupdate.com/members/daily/Art012602.htm>, Printed Aug. 21, 2006.

* cited by examiner

TRANSVERSE SUSPENSION DEVICE

CROSS-REFERENCE TO RELATED APPLICATIONS

This application claims priority to International Patent Application No. PCT/GB03/01606 filed Apr. 13, 2003, the complete disclosure of which is herein incorporated by reference for all purposes.

The present invention relates to a transverse suspension device, in particular, but not exclusively, a transverse suspension screw for anterior cruciate ligament (ACL) fixation in the femoral tunnel.

Transverse securing devices are being increasingly used for secure fixation of ACL replacement grafts in the femoral tunnel during ACL reconstruction surgery. One such device known as the bone Mulch™ screw is available from Arthrotek®.

The bone mulch screw has a hollow body section with an opening at either end thereof. The tip of the screw is stepped having a sharp narrow leading section followed by a slightly wider trailing section. The trailing end of the tip is joined to the body section on one side of the said body section only, leaving a gap at the leading end of the body section so that bone mulch material can be forced therethrough and into the femoral tunnel after fixation. A suture passing loop must be located over the end of the partially inserted tip in the femoral tunnel and it is for this reason that the tip is stepped so that the leading end is as narrow as possible to maximise efficiency in the difficult step of locating a suture loop over the leading end of the bone mulch tip when it first protrudes into the femoral tunnel. Once the suture loop is in position, the bone mulch screw may be advanced further so that the stepped tip bores through the medial wall of the femoral tunnel until the thicker section of the tip fully extends transversely across the tunnel. The graft may then be pulled into the tunnel by passing it over the transverse pin after attaching it to one end of the looped suture and pulling the other end. Unfortunately, because the graft must be pulled over the pin at the blind end of the femoral tunnel it is necessary to ream out bone from inside the femoral tunnel so as to create sufficient space for the graft to be pulled over the pin without becoming caught between the end of the femoral tunnel and the pin. By reaming out bone from the end of the femoral tunnel, the compression of the graft against the tunnel wall is decreased lengthening the process of healing and fixation. Furthermore, the looping of the suture is not a straightforward step and requires an arthroscopic view via the tibial tunnel and may also require several attempts before the loop is successfully located over the leading end of the tip.

Alternatives to such transverse suspension pins include interference cross pins which interfere against a bone block in bone-patella tendon-bone graft fixation. A suitable device for such procedures is the BiLok™ screw. However, such techniques are not appropriate for pure tendon grafts such as the double-looped semitendinosus and gracilis (DLSTG) hamstring graft which is one of the strongest and stiffest grafts available and does not suffer from a number of complications associated with the bone-patella tendon-bone graft.

According to a first aspect of the present invention there is provided a transverse suspension device for ACL graft fixation in a femoral bone tunnel comprising a body section and a smooth head section forming the leading end of the device, the body and smooth head sections each being cannulated along the entire lengths thereof; the head section comprising a recess-engaging section extending proximally from the distal end thereof and operable to engage with a recess formed in the bone tunnel, and a graft loop support section between the recess-engaging section and the body section adapted to stably support the graft loop thereover.

By the term stably support, is meant that the portion of the graft loop located over the loop support section is prevented from movement along the longitudinal axis of a femoral or other bone tunnel in which the device is located transverse thereto.

Preferably, the body section has a wider cross-section than the graft loop support section to provide an abutment surface at the proximal end of the graft loop support section. Preferably, the abutment surface provides a graft abutment in use, to urge the graft loop into contact with the opposite wall of a bone tunnel.

Advantageously, in use, the said abutment surface urges the graft loop onto the opposite wall of the femoral tunnel and thus the bone and the graft loop are encouraged to graft to each other.

Therefore, according to a second aspect of the present invention there is provided a transverse suspension device for ACL graft fixation in a femoral bone tunnel comprising a body section and a smooth head section forming the leading end of the device, the body and smooth head sections each being cannulated along the entire lengths thereof; the head section comprising a recess-engaging section extending proximally from the distal end thereof and operable to engage with a recess formed in the bone tunnel, and an abutment surface located between the body section and the recess-engaging section adapted to urge the graft against the opposite wall of the bone tunnel in use.

Preferably in relation to the second aspect of the present invention the transverse suspension device comprises a graft loop support section which is, preferably, adapted to stably support the graft loop thereover. Preferably, the graft loop support section is located between the recess-engaging section and the body section.

Preferably, the graft loop support section is of constant, preferably, circular, cross section. Typically, the head section is located on the same longitudinal axis as the body section.

Preferably, at least a part of the recess-engaging section tapers outwardly from the leading end thereof. Preferably, the recess-engaging section comprises a rounded nose section at the leading end thereof which, preferably, terminates the tapered section at the leading end of the device. Preferably, at least the major part of the recess-engaging section is frusto-conical.

Preferably, the device is cannulated along the entire length thereof. Preferably, the head section extends distally from the distal end of the body section.

Preferably, the body section is suitably adapted for secure fixation, in use, in a tunnel transverse to the femoral tunnel, preferably, by interference with the tunnel wall. For instance, the body section may comprise a series of external protrusions such as ribs extending along the body section but tapering outwardly towards the trailing end to prevent the head of the device coming out of the femoral tunnel. Preferably, however, the body section is externally threaded so that the device may be conveniently screwed into position.

Preferably, the body section protrusions or threads provide a larger dimension for the body section between smaller dimension areas and, preferably, at least the larger dimension cross-section is wider than the dimension of the graft loop support section, more preferably, the smaller dimension cross-section areas of the body section are also wider than the graft loop support section.

As mentioned above, preferably, at least a part of the smooth head tapers outwardly from the leading end thereof to form a tapered section of the head. The smooth head may also include a non-tapered section between the tapered section and the body section previously described as the graft loop support section. Preferably, the widest diameter of the smooth head is less than the outer diameter of the body section. Preferably, the body section itself is not tapered but has a substantially uniform overall diameter along the length thereof subject to thread undulations or protrusions on the exterior surface thereof. The cannulated interior of the device may be wider at its trailing end to accommodate a suitable fixation device to assist location of the device in position.

Advantageously, by having the body and head section, cannulated, the device may be advanced along a guide wire and located under the loop of a graft pre-positioned in the femoral tunnel. An additional advantage is provided by the tapered head section which increasingly compresses the graft as it advances thereunder during fixation. A threaded or ribbed body section may still further compress the graft forwards and outwards when the smooth head is short enough to completely advance beneath the first loop so that then the body section impinges on the graft directly. However, compression is chiefly effected by an abutment surface at the distal end of the body section. Preferably, the abutment surface is in the form of a flange, which is, preferably, annular. Graft compression advantageously contributes to graft incorporation by assisting tunnel wall bonding of the graft. The abutment surface may be a flange.

Therefore, according to a third aspect of the present invention there is provided a method of ACL graft ligament fixation comprising the steps of:

forming a femoral tunnel for graft fixation therein;

forming a transverse tunnel for intersecting the femoral tunnel;

locating a graft loop in the femoral tunnel in such a manner that the open face of the loop faces the intersection of the transverse tunnel, passing at least a part of the head section of a transverse suspension device according to the first or second aspect of the present invention through the graft loop via the transverse tunnel.

By passing the smooth head of the device through the graft loop, the graft is progressively compressed outwardly against the femoral tunnel walls before being stably located therein via the graft loop support section.

Preferably, after location of the graft loop in the femoral tunnel, a guide wire is advanced thereunder from the transverse tunnel using a suitable viewing device such as an arthroscope. The suspension device may then be passed along the guide wire.

Preferably, a dilation device is passed along the guide wire prior to the suspension device to dilate the loop in the graft after the guide wire is advanced thereunder, and, preferably, the dilation device is forced into the opposite wall of the femoral tunnel to create a recess therein.

The dilation device may then be removed and the suspension device may then be passed along the guide wire.

Preferably, the suspension device is advanced under the graft loop. Preferably, the recess-engaging section is advanced into the recess in the opposite wall of the femoral tunnel and, preferably, the body section is advanced into the femoral tunnel. Preferably, the abutment surface of the body section urges the graft loop onto the opposite wall of the femoral tunnel.

Advantageously, the insertion of the dilation device opens the graft loop allowing the suspension device to pass freely thereunder.

Advantageously, the smooth surface of the head section prevents damage to the graft during its fixation and the method of locating the head section under the loop avoids the need for complex suture loop passing and looping steps. Furthermore, because the head section compresses the graft loop directly against the walls of the femoral tunnel in a single step, damage to the graft is minimised.

Preferably, the head of the device is advanced as far as the opposite wall of the femoral tunnel. The head may also be advanced into the opposite tunnel wall a short distance to provide more secure fixation, if required.

However, as the cannulation extends through the head section the leading tip of the head section does not typically terminate in a sharp point but is typically rounded into a convex tip with a centrally disposed cannular hole.

Preferably, the diameter of the cannular hole at the tip of the device is in the range 0.1-3 mm, more preferably 0.5-1.5 mm, most preferably 0.8-1.2 mm.

Preferably, the diameter of the cannular hole at the trailing end of the device is between 0.1-15.0 mm, more preferably 1-10 mm, most preferably 2-8 mm.

Preferably, the length of the head section is between 1-25 mm, more preferably between 2-20 mm, most preferably between 5-15 mm.

Preferably, the length of the body section is between 5-50 mm, more preferably between 10-40 mm, most preferably between 20-30 mm.

Preferably, the maximum width of the head section is between 1-15 mm, more preferably between 2-8 mm, most preferably, between 3-8 mm. An especially preferred width is 5-7 mm.

Preferably, the width of the body section excluding any protrusions is between 2-15 mm, more preferably, between 3-12 mm, most preferably 5-12 mm.

Preferably, the minimum width of the graft loop support section of the head section, is between 0.5-10 mm, more preferably, between 2-8 mm, most preferably, between 2-5 mm.

Preferably, the trailing end of the device is adapted to receive a suitable tool for use during fixation of the device. The tool is preferably suitable to locate the device in the transverse tunnel via a push fit or screw fit mechanism.

An embodiment of the invention will now be described by way of example only and with reference to the accompanying drawings in which.

Figure 1:
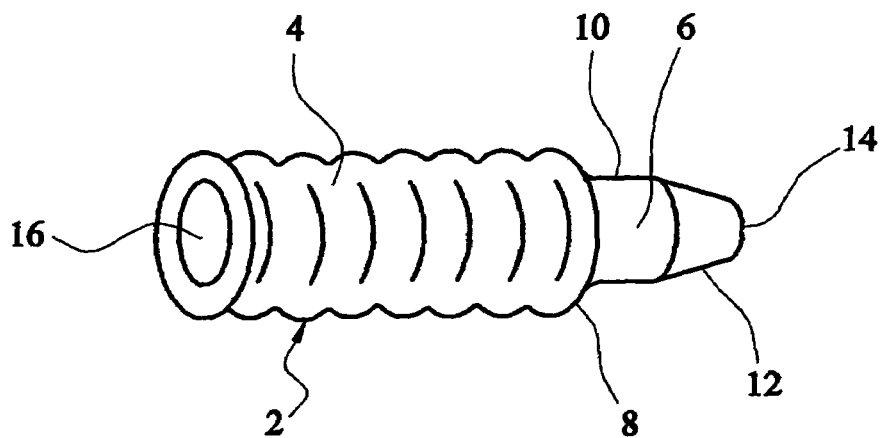
FIG. 1 is a perspective view of a transverse suspension device in accordance with the present invention.
Figure 2:
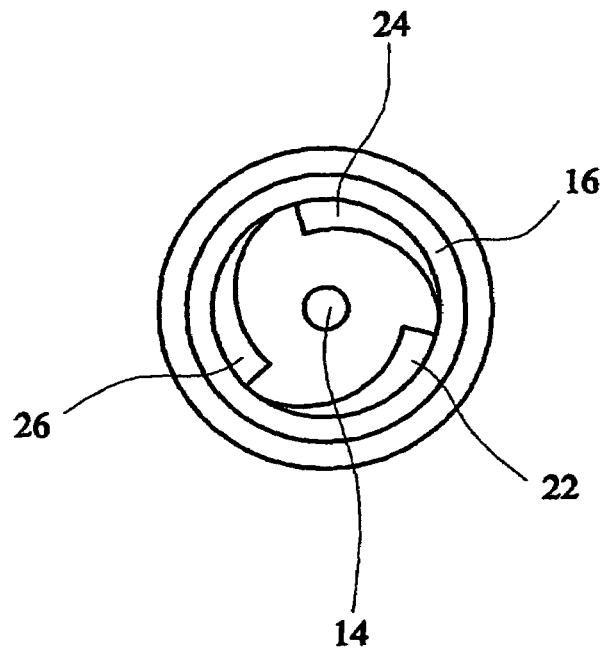
FIG. 2 is a trailing end view of the transverse suspension device of FIG. 1.
Figure 3:
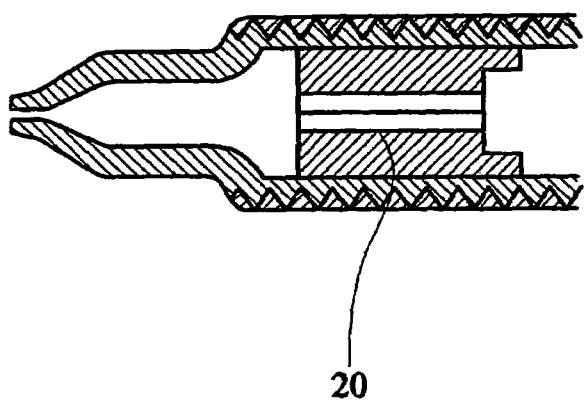
FIG. 3 is a sectional view through the transverse suspension device of FIG. 1.

Referring to FIGS. 1, 2 and 3, a transverse suspension device 2 has a tubular body section 4 and a co-axial head section 6 joined to and protruding from the leading end 8 of the body section 4. The transverse suspension device 2 is cannulated along the length of the axis thereof so that it may be passed along a guide wire in use. The body section 4 is externally screw threaded along its entire length and the head section 6 includes a trailing part 10 coaxial with the body section 4 but of a narrower outer diameter and a frustoconical nose section 12 extending from the leading end of the trailing part 10 and having the narrower end forming the leading end of the nose section. The tip of the nose section is rounded in a convex manner and includes the exit port 14 of the cannulated hole of the device at its centre.

The hollow interior of the device extends from the trailing end in the form of a central tubular recess 16 which is stepped into a radially narrower keyhole section 20, midway along the length of the body section, which extends forwardly through the remainder of the body section as far as the leading end thereof. The keyhole section 20 includes three radially inwardly directed longitudinally extending vanes 22, 24 and 26. The vanes are equally circumferentially spaced apart around the interior wall of the tube but have their wailing ends slightly axially recessed with respect to the beginning of the keyhole section. Each vane has a leading face which is arcuate in end section and a trailing face which is substantially flat in end section and extends radially away from the longitudinally extending apex of the vane back to the internal circumferential wall of the hollow keyhole section. Thus, each vane farms a radially inwardly directed ridge which ridge extends longitudinally along the length of the keyhole section and provides the means for a suitable co-engaging tool to engage therewith for screwing the device into position during surgery.

Figure 4:
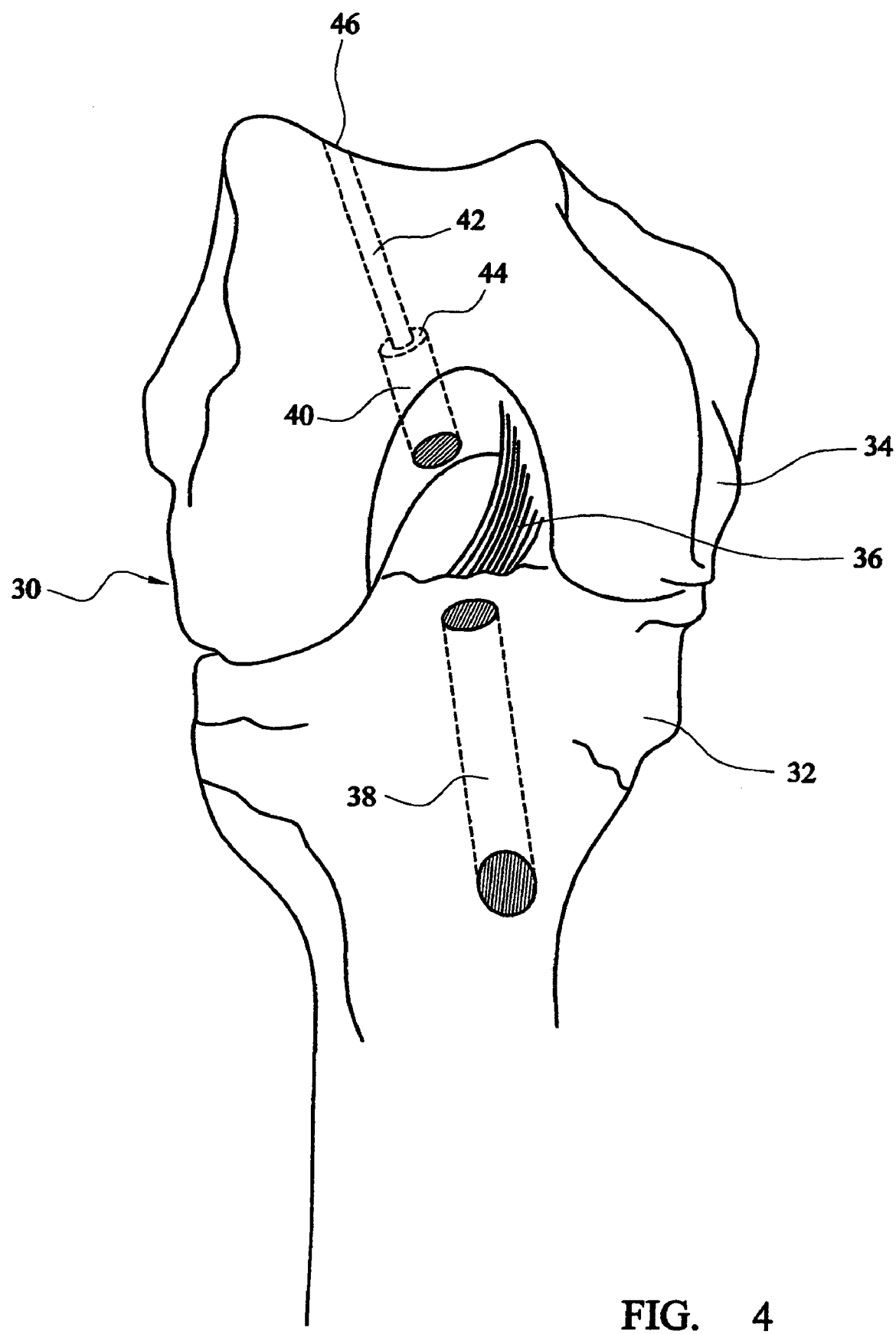
FIG. 4 is a partial view of the right knee joint showing the femoral and tibial tunnels prepared for ACL reconstruction.

Referring to FIG. 4, a partial view of the right knee joint 30 includes a tibia section 32 and a femur section 34 articulating therewith in the usual manner. In the illustration shown, the posterior cruciate ligament 36 is shown extending between the tibia and the femur but the anterior cruciate ligament is missing. A tibial tunnel 38 of standard construction extends between the anterior surface of the tibia and the tibial plateau. A femoral tunnel 40 extends from the intracondylar notch towards the lateral femoral aspect and includes a passing pin tunnel 42 which extends from the proximal end 44 of the femoral tunnel to exit at the lateral femoral aspect of the femur 46. The method of preparation of the tibial and femoral tunnels are in accordance with standard techniques known in the art.

Figure 5:
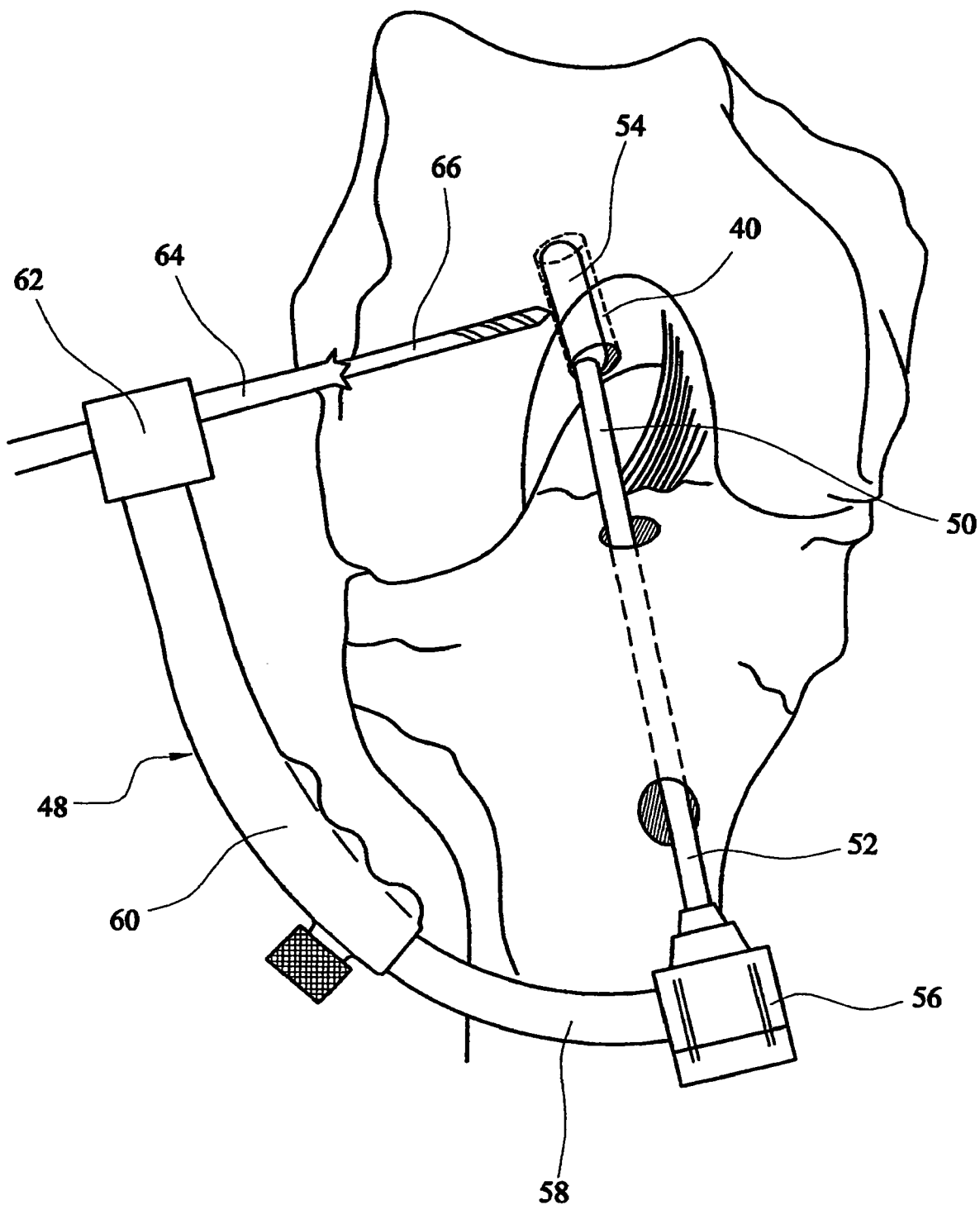
FIG. 5 is a partial view of the right knee joint illustrating the use of an A-Tech guide.

Referring to FIG. 5, a transverse femoral guide 48 of known construction includes a femoral locator 50 comprising an elongate straight rod 52 with a femoral locator head 54 located at the proximal end thereof and which is sized to fit within the femoral socket 40. The straight rod section 52 is designed to extend from an anchor section 56, through the tibial tunnel and intercondylar notch. An arcuate guide arm 58 of standard construction extends from the lateral side of the anchor 56 in an arcuate manner and includes an adjustable sleeve section 50 for multiple position fixation with respect thereto. The head 62 of the guide arm sleeve 60 accommodates a cannulated guide wire bullet 64 which extends therethrough. The positioning of the head of the sleeve 62 is such that it extends parallel with the femoral locator head 54 and the cannulated bullet extends through an appropriately sized perpendicular aperture in the head of the guide arm sleeve 62 so that it may be advanced towards the head of the femoral locator. In use, a small lateral incision is made on the surface of the knee joint to remove any soft tissue so that the cannulated bullet may be advanced until it firmly locates on the lateral epicondyle. The length of the transverse tunnel to be drilled can be determined from the measurements on the transverse bullet according to known techniques. The 2.4 mm guide wire may then be drilled through the femur until it touches the femoral locator. Thereafter, the guide 48 may be removed together with the femoral locator leaving the guide wire 66 in position. The guide wire 66 is then advanced to penetrate bone on the opposite wall of the femoral tunnel by approximately 1 cm.

Figure 6:
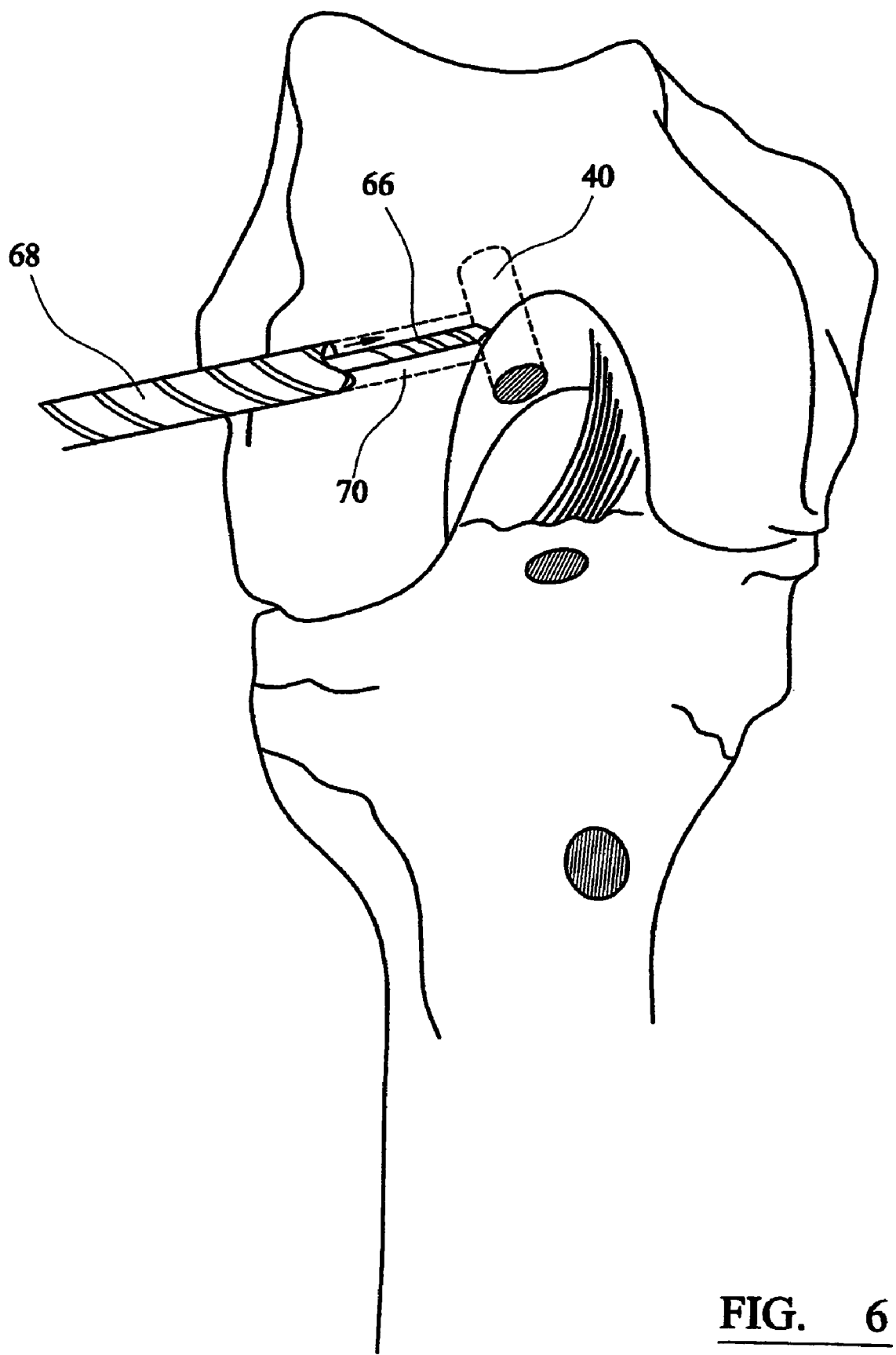
FIG. 6 is the view of FIG. 4 showing the drilling of the transverse tunnel.

Referring to FIG. 6, the guide wire 66 is shown as it is being advanced towards the opposite wall of the femoral tunnel. Thereafter, it may be over drilled with an 8 mm cannulated drill 68 to create the transverse tunnel 70 which intersects with the femoral tunnel 40. An arthroscope (not shown) may be inserted into the femoral tunnel via the intercondylar notch to assess penetration of the drill 68 into the femoral socket, as the drill should not penetrate the opposite wall of the femoral socket. At this point in the procedure, the 2.4 mm guide wire pin 66 may be removed and replaced with a thinner 1 mm guide wire of the transverse screw. Thereafter, the cannulated drill 68 may be removed.

Figure 7:
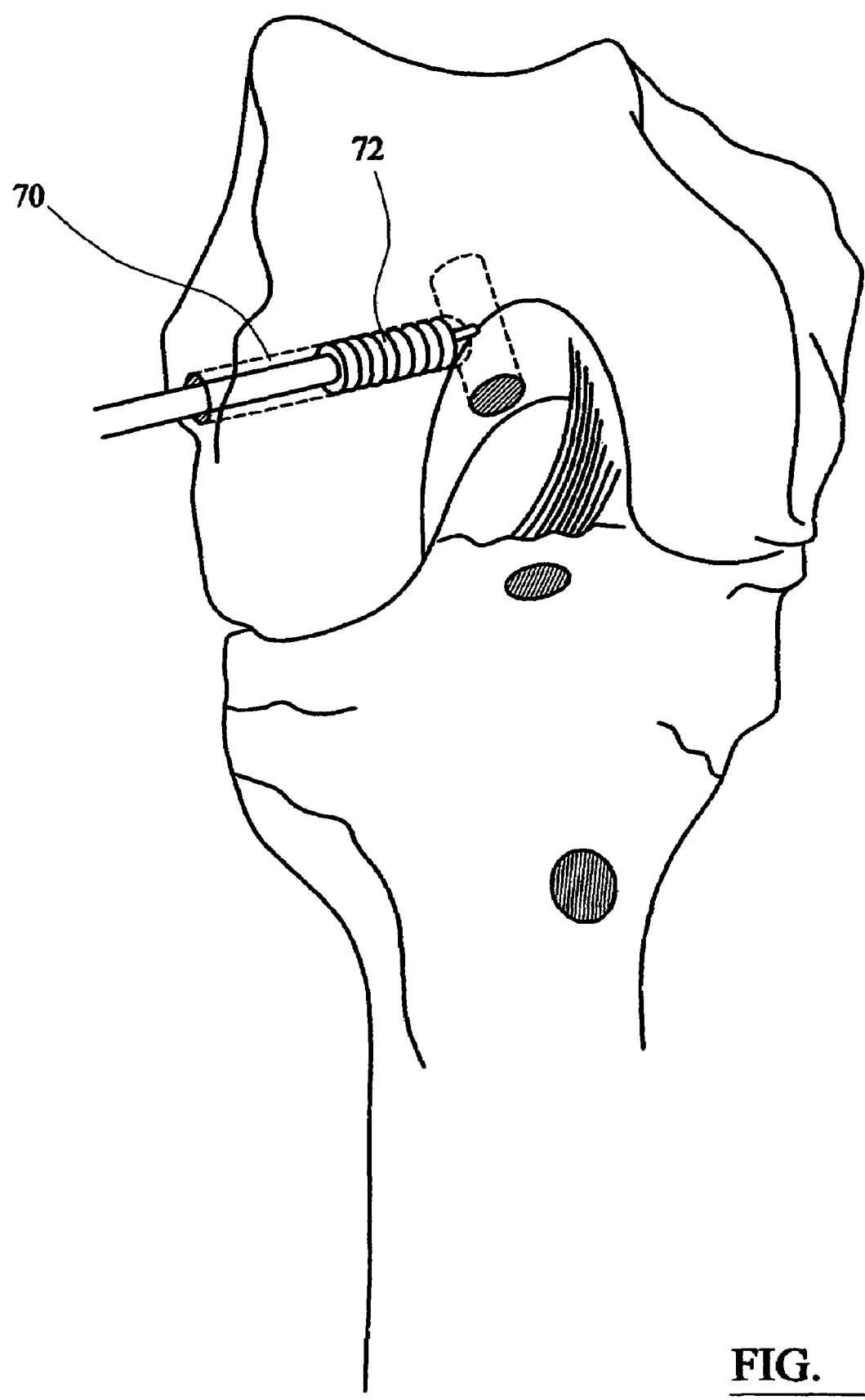
FIG. 7 is a view of FIG. 4 showing the guide wire and tap in position.

Referring to FIG. 7, a cannulated tap 72 is shown being advanced along the transverse tunnel 70 so as to pre-thread the tunnel in preparation for receiving the transverse suspension device screw. After tapping of the transverse tunnel 70 is complete, the tap 72 may be removed leaving the guide wire in position. The guide wire is then retracted away from the medial wall of the femoral tunnel to provide a gap which is sufficient to allow insertion of the graft into the femoral tunnel.

Figure 8:
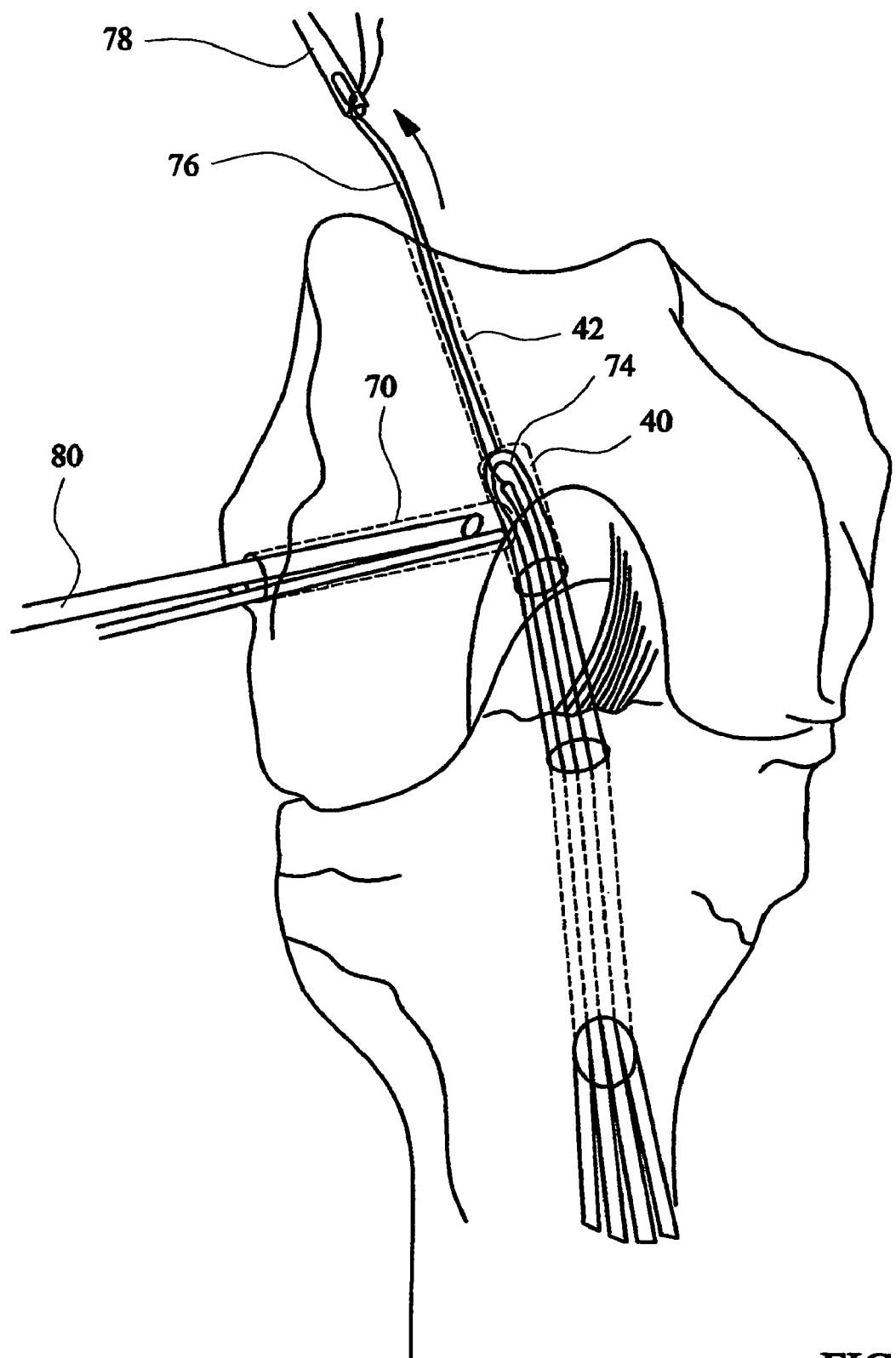
FIG. 8 is a view of FIG. 4 showing the graft being pulled into position.

Referring to FIG. 8, a graft loop 74 is shown located in position in the femoral tunnel 40. The graft includes sutures 76 threaded therethrough and tied at the proximal end to the end of a passing pin 78. In practice, the passing pin is advanced through the tibial tunnel, intracondylar notch and femoral tunnel and passed out through the passing pin tunnel 42 to appear at the lateral femoral aspect. The sutures may then be pulled to locate the loop of the graft in the correct position in the femoral tunnel. Care should be taken so that the face of the loop faces the intersection with the transverse tunnel 70. The screw guide wire extending down the transverse tunnel 70 may then be located under the loop using an arthoscope 80 via the same transverse tunnel 70. The arthoscope 80 and guide wire may be advanced together under the loop and once successively located the arthoscope may be retracted and removed taking care to retain the guide wire in position.

Figure 9:
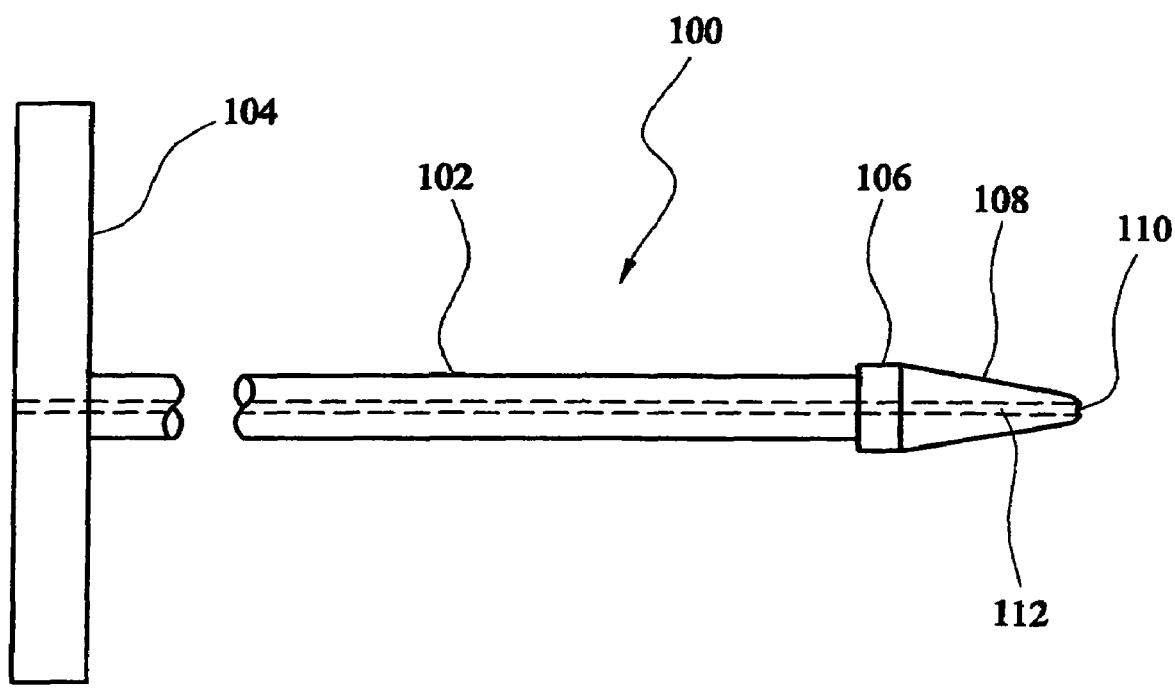
FIG. 9 is a cross sectional view of a dilation device.

Referring to FIG. 9, a dilation device 100 is shown having a tubular shaft 102, a handle section 104 and a nose section 108. The nose section 108 is frustoconical in shape, and has a rounded leading end 110. The frustoconical section extends distally from a shoulder section 106 at the trailing end thereof, the said shoulder section extending proximally with a constant cross-section as far as the shaft 102, co-axial therewith but of a slightly larger cross-section than the shoulder. The dilation device 100 is cannulated 112 along the entire length thereof so as to be passed along the guide wire such that it dilates the graft loop 74 as it passes transversely through the bone tunnel. The dilation device 100, is advanced along the guide wire with sufficient force to create a recess in the opposite wall of the femoral tunnel in which the frustoconical nose section 12 of the suspension device 2 may be accommodated. Accordingly, the dilation device is suitably dimensioned to be complimentary to the suspension device in this respect. The dilation device 100 is then retracted leaving the graft loop 74 sufficiently dilated such that the suspension device 2 can be advanced therethrough. When retracting the dilation device 100, care is taken to retain the guide wire in position.

Figure 10:
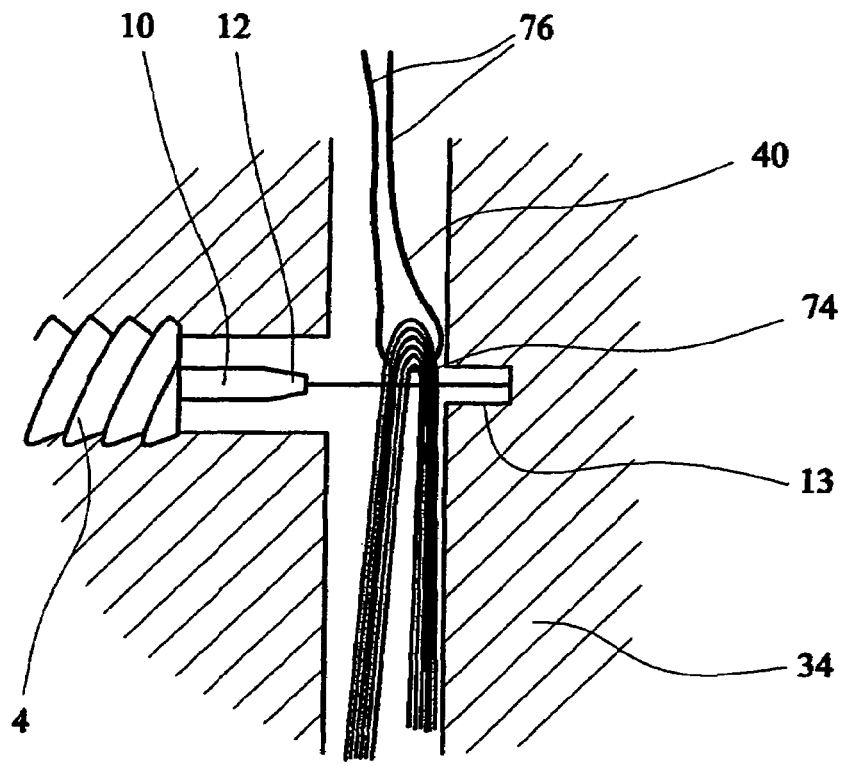
FIG. 10 is a cross sectional view of the femoral tunnel prior to location of the suspension device.

Referring to FIG. 10, the cannulated screw is shown located over the guide wire and advancing towards the dilated graft loop 74

Figure 11:
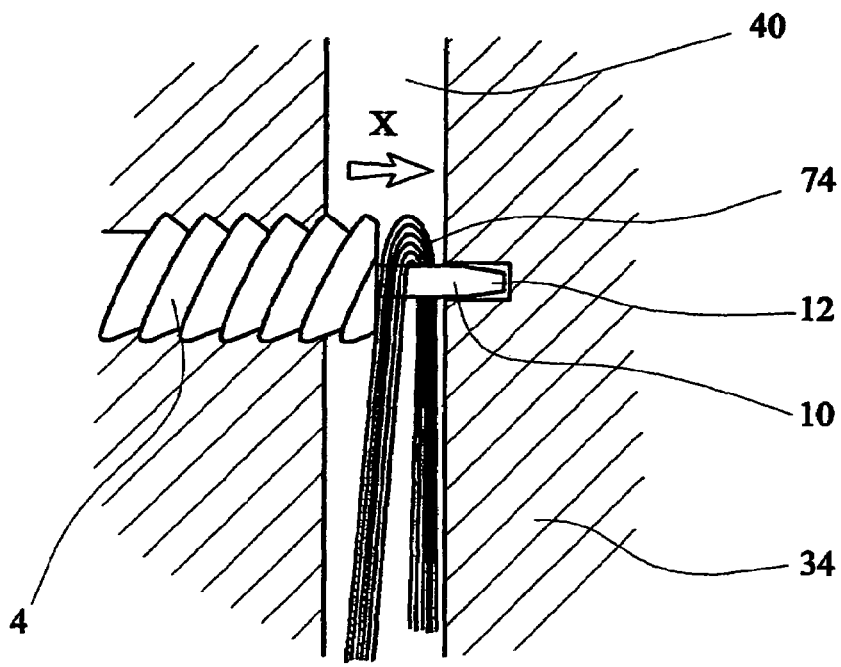
FIG. 11 is a cross sectional view of the femoral tunnel with the suspension device in place.

Referring to FIG. 11, the suspension device 2 is shown fully advanced into the femoral tunnel with its frustoconical nose section 12 embedded in the recess 13 formed in the opposite wall of the femoral tunnel. The body section 4 being of a wider diameter than the trailing part of the head section 6, provides an annular abutment for the graft loop residing on the trailing part 10 and as the suspension device advances the annular abutment urges the graft loop against the opposite wall of the bone tunnel thus encouraging the graft and the bone to graft to each other.

Figure 12:
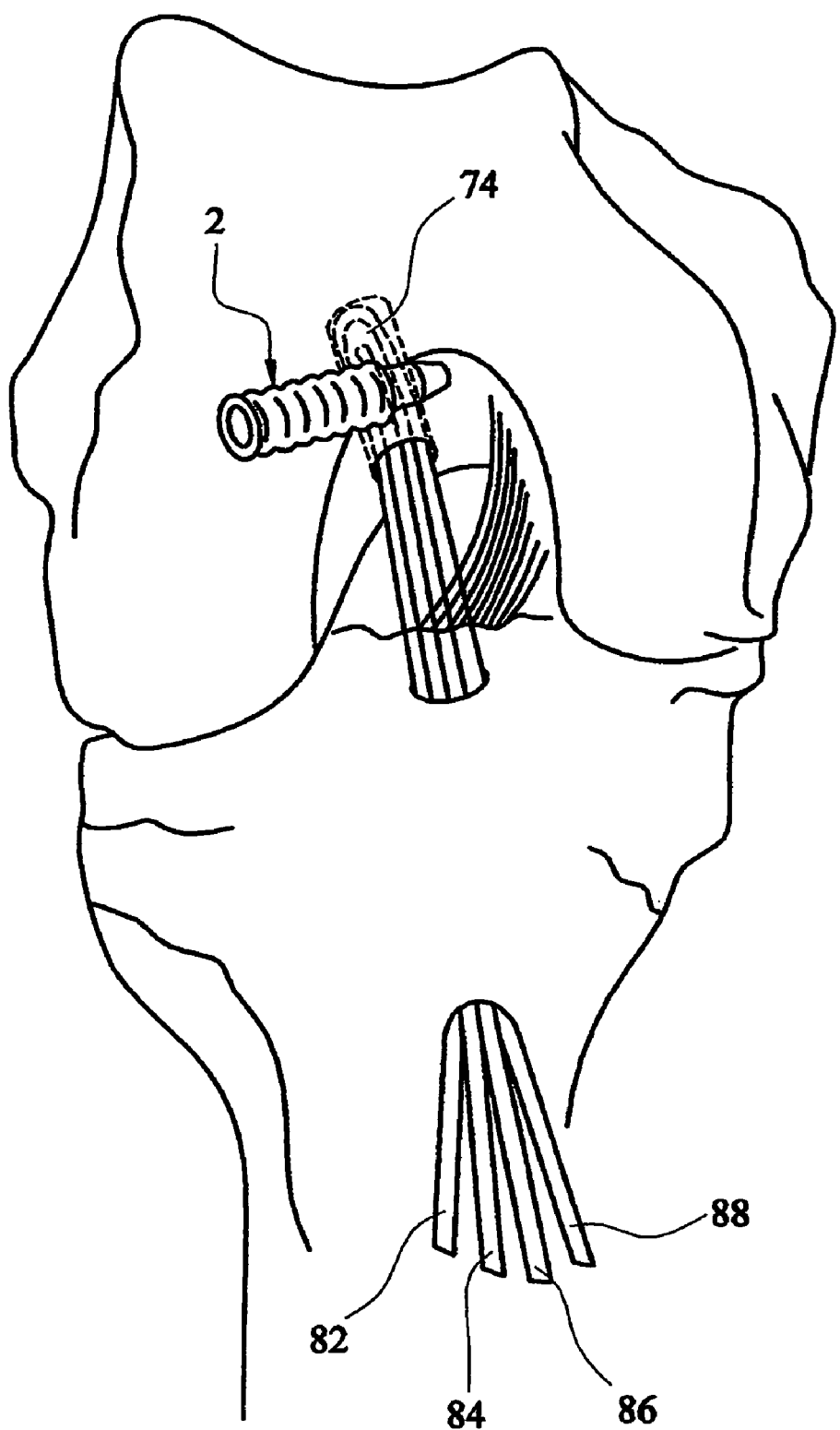
FIG. 12 is a view of FIG. 4 showing the transverse suspension device stably securing the graft loop in the femoral tunnel.

Thereafter, the guide wire may be removed. The final position of the cannulated transverse suspension device screw is shown in FIG. 12 with the outer wall of the head of the screw and the leading end of the body section urging the graft into contact with the walls of the femoral tunnel. The trailing ends of the graft 82, 84,86, 88 may be fixed to the tibia in accordance with the surgeons preference and in accordance with techniques known in the art.

A suitable type of graft for use with the present invention is a double-looped semitendinosus and gracilis (DLSTG) hamstring graft which may be prepared in accordance with techniques known in the art.

A suitable material for the screw would be a combination of ceramic and polymer materials. A suitable ceramic component could be tri-calcium phosphate or ceramic hydroxyapetite. However, any suitable bio ceramic may be used. The polymer component may incorporate poly lactic acid to provide good biocompatibility.

The reader's attention is directed to all papers and documents which are filed concurrently with or previous to this specification in connection with this application and which are open to public inspection with this specification, and the contents of all such papers and documents are incorporated herein by reference.

All of the features disclosed in this specification (including any accompanying claims, abstract and drawings), and/or all of the steps of any method or process so disclosed, may be combined in any combination, except combinations where at least some of such features and/or steps are mutually exclusive.

Each feature disclosed in this specification (including any accompanying claims, abstract and drawings), may be replaced by alternative features serving the same, equivalent or similar purpose, unless expressly stated otherwise. Thus, unless expressly stated otherwise, each feature disclosed is one example only of a generic series of equivalent or similar features.

The invention is not restricted to the details of the foregoing embodiment(s). The invention extends to any novel one, or any novel combination, of the features disclosed in this specification (including any accompanying claims, abstract and drawings), or to any novel one, or any novel combination, of the steps of any method or process so disclosed.

What is claimed is:

1. A method of ACL graft ligament fixation comprising the steps of:
    forming a passing pin tunnel in a femur, said passing pin tunnel having a longitudinal axis and exiting a superior wall of the femur;
    forming a femoral tunnel along said longitudinal axis, said femoral tunnel having a larger diameter than said passing pin tunnel and terminating in said femur;
    forming a transverse tunnel intersecting the femoral tunnel, said transverse tunnel terminating within said femur;
    locating a graft loop in the femoral tunnel in such a manner that an open face of the loop faces an intersection where the femoral tunnel intersects the transverse tunnel, and wherein said locating comprises pulling on sutures holding said graft loop to locate said graft loop, and said pulling on sutures comprises pulling on said sutures through said passing pin tunnel;
    forming a recess in an opposite wall of the femoral tunnel; and
    passing a head section of a transverse suspension device through the graft loop via the transverse tunnel such that said head section completely advances beneath said graft loop and until said head contacts the opposite wall of the femoral tunnel and urging said graft loop against said opposite wall as at least a part of said head is embedded in said recess, and wherein a portion of said graft loop is compressed forward and outward between said opposite wall and an abutment surface of the transverse suspension device, wherein the abutment surface comprises an annular flange having a wider diameter than said head section.

2. A method according to claim 1, wherein after location of the graft loop in the femoral tunnel, a guide wire is advanced thereunder from the transverse tunnel.

3. A method according to claim 2, wherein the suspension device is passed along the guide wire after the guide wire is advanced under the graft loop.

4. A method according to claim 1, wherein the head of the device is advanced as far as a distal head of the recess formed in the opposite wall of the femoral tunnel.

5. A method of ACL graft ligament fixation comprising the steps of:
    inserting a transverse suspension device comprising a proximal body section defining a longitudinal axis, a head section extending along said longitudinal axis and protruding distally from the body section, said head section having a smaller diameter than that of said body section, a nose section distal to and distinct from said head section and having a reduced diameter as compared to said head section, said nose section extending along said longitudinal axis, and an annular abutment surface distinct from said head section and disposed between said head section and said body section wherein said abutment surface comprises an annular flange and is substantially at an angle to said longitudinal axis;
    forming a femoral tunnel;
    forming a transverse tunnel intersecting the femoral tunnel;
    locating a graft loop in the femoral tunnel in such a manner that an open face of the loop faces an intersection where the femoral tunnel intersects the transverse tunnel; and
    passing at least a part of said nose section and said head section of said transverse suspension device through the graft loop via the transverse tunnel such that said head section completely advances beneath said graft loop and urging the graft loop against an opposite wall of the femoral tunnel until said nose section is embedded in a recess formed in the opposite wall of the femoral tunnel wherein a portion of said graft loop is compressed forward and outward between said annular flange and said opposite wall and such that said ligament is supported by said head section.

6. A method according to claim 2, wherein said guidewire is advanced under observation with a viewing device.

7. A method of claim 6 wherein said viewing device is an arthroscope.

8. A method of claim 5 wherein said nose section is frustoconical shaped.

9. A method of claim 5 wherein said transverse suspension device is cannulated.

10. A method of claim 5 wherein the recess is formed with a dilator tool.

11. A method of claim 5 wherein said transverse tunnel is drilled to intersect and not cross said femoral tunnel.

12. A method of claim 5 wherein said body section comprises external threads.

13. A method of ACL graft ligament fixation comprising the steps of:
   inserting a transverse suspension device comprising a threaded tubular body section defining a longitudinal axis, a frustoconical head section extending along said longitudinal axis and protruding distally from the body section, said head section having a smaller diameter than that of said body section, and an annular abutment surface disposed between said head section and said body section wherein said abutment surface comprises an annular flange is substantially at an angle to said longitudinal axis;
   forming a femoral tunnel;
   forming a transverse tunnel intersecting the femoral tunnel but not extending beyond said femoral tunnel such that said femoral tunnel comprises an opposite wall;
   forming a recess in said opposite wall with a dilator tool;
   locating a graft loop in the femoral tunnel in such a manner that an open face of the loop faces an intersection where the femoral tunnel intersects the transverse tunnel;
   passing a head section of a transverse suspension device through the graft loop via the transverse tunnel such that said head section completely advances beneath said graft loop and urging the graft loop against the opposite wall until at least a part of said head section is embedded in said recess and wherein a portion of said graft loop is compressed forward and outward between said annular flange and said opposite wall, and wherein said passing is performed subsequent to said locating.

14. A method according to claim 5, wherein said angle is about 90 degrees.

15. A method according to claim 5, wherein said head section has a substantially constant diameter.

* * * * *